United States Patent [19]

Malchesky et al.

[11] Patent Number: 5,518,927
[45] Date of Patent: May 21, 1996

[54] INSTRUMENT STERILATION LIFE-SPAN INDICATOR

[75] Inventors: Paul S. Malchesky, Painesville Township; George E. Grignol, Mentor, both of Ohio

[73] Assignee: Steris Corporation, Mentor, Ohio

[21] Appl. No.: 291,989

[22] Filed: Aug. 17, 1994

[51] Int. Cl.⁶ .................................................. G01N 31/22
[52] U.S. Cl. .................... 436/1; 422/28; 422/58; 422/61
[58] Field of Search .................. 422/28, 56–58, 422/61; 436/1–2

[56] References Cited

U.S. PATENT DOCUMENTS

| | | | |
|---|---|---|---|
| D. 305,386 | 1/1990 | Rams et al. | D4/104 |
| 3,471,422 | 10/1969 | Edlein et al. | 436/1 |
| 3,966,414 | 6/1976 | Khattab et al. | 436/1 |
| 3,999,946 | 12/1976 | Patel et al. | 436/2 |
| 4,121,714 | 10/1978 | Daly et al. | 436/1 |
| 4,382,063 | 5/1983 | Romito et al. | 422/57 |
| 4,407,960 | 10/1983 | Tratnyek | 436/1 |
| 4,802,255 | 2/1989 | Breuer et al. | 15/159 A |

*Primary Examiner*—Lyle A. Alexander
*Attorney, Agent, or Firm*—Fay, Sharpe, Beall, Fagan, Minnich & McKee

[57] ABSTRACT

A pigment such as crystal violet is impregnated in or otherwise affixed to a translucent plastic or porous member (14, 22). The color change material changes at least one of opacity or color with repeated exposure to a fluid sterilant, such as an oxidant solution. A label (10, 24) is mounted behind the translucent plastic material and carries an indicia (12, 26). With repeated sterilizations of the instrument, the color change material becomes progressively more translucent, allowing the indicia to be read through the translucent plastic material. When the indicia becomes visible, such as after about 7 sterilization cycles in FIG. 3, the user is warned to discontinue use of the instrument, either discarding it or having it rebuilt. Rather than having a written indicia, a color scale (30) can be provided for comparison against the current color of the color change material. When the color changes to the discard color on the color scale, the user is again advised to discontinue use of or rebuild the instrument.

19 Claims, 3 Drawing Sheets

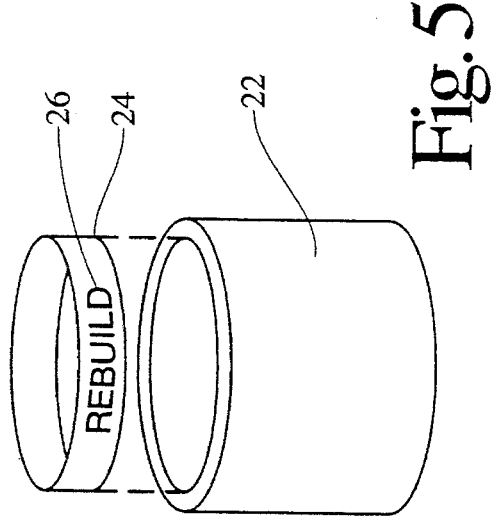
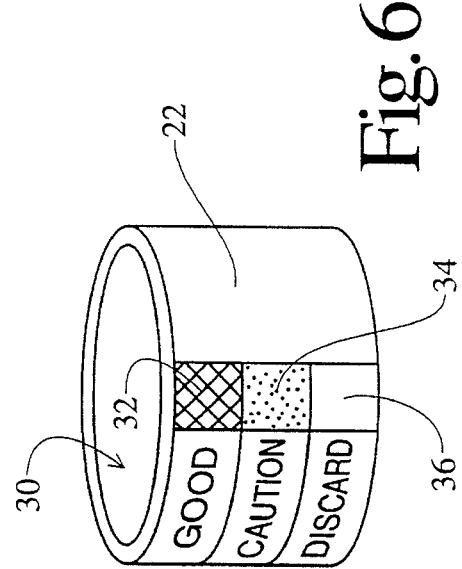
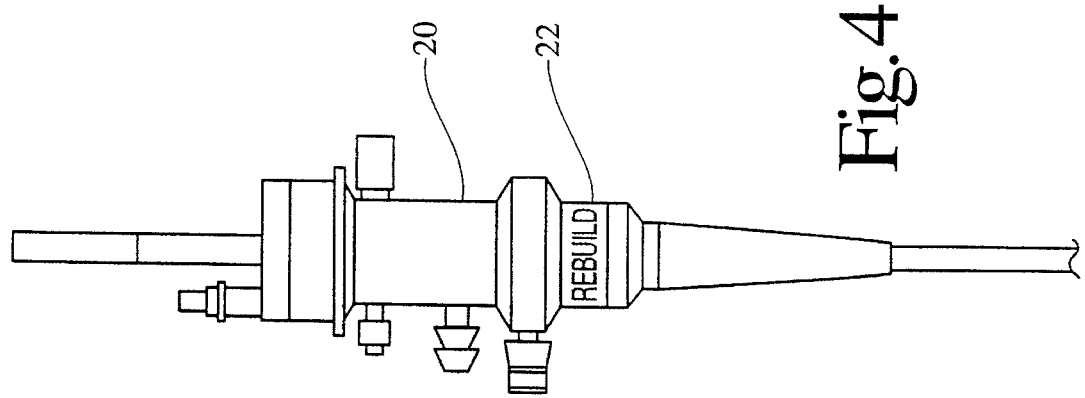

INSTRUMENT STERILATION LIFE-SPAN INDICATOR

BACKGROUND OF THE INVENTION

The present invention relates to the microbial decontamination and medical equipment maintenance arts. It finds particular application in conjunction with counting a number of strong oxidant sterilization cycles to which medical (including dental and surgical) equipment has been subjected and will be described with particular reference thereto. However, it is to be appreciated that the invention will also find application in conjunction with monitoring the number of times that mortuary, laboratory, and other equipment have been sterilized or disinfected, monitoring other processing cycles of both medical and non-medical equipment, and the like.

Sterilizing or disinfecting equipment subjects articles to an environment which kills microbes. Common sterilizers include a steam autoclave which subjects the items to a combination of high temperature and pressure. Ethylene oxide gas sterilizers subject the items to reactive, ethylene oxide gas. Liquid sterilizers treat the items with a liquid solution that includes a reactive component, such as a strong oxidant.

Not all regularly sterilized medical instruments are made of materials which are substantially immune to the high temperature and pressure of a steam autoclave. Many instruments have plastic or rubber components which cannot withstand the thermal and pressure stresses of a steam autoclave. These items are typically sterilized using low temperature fluid (gas or liquid) sterilization systems.

Many instruments are rated to have a limited useful life. One scale for measuring the useful life is the number of sterilization cycles. After a preselected number of sterilization cycles, the instrument no longer has an assured functionality and should be discarded or rebuilt.

The loss of assured functionality may be attributable to various causes including dulling of cutting edges, potential misalignment of parts or wobble in joints, degradation of parts, particularly plastic and rubber parts, from use or the microbial decontamination processing or the like. The high temperatures of steam sterilization or reaction with gas or liquid sterilants may degrade some plastic and rubber parts. Such plastic and rubber components may cumulatively become bleached, brittle, or tacky.

Heretofore, difficulty was encountered in determining whether the functionality of the instruments was compromised. Degradation of internal parts is not readily determined by visual observation. Some degradation, such as becoming brittle or dull is hard for a human observer to gauge. Various techniques have been tried, but each has significant drawbacks. Periodic disassembly is time consuming and is not available for all instruments. Counting the number of use/sterilization cycles is often unreliable, particularly when there are multiple users and multiple copies of each instrument. Inventory control and purchase date monitoring does not provide a reliable indication of the number of use and sterilization cycles.

The present invention provides a new and improved technique for monitoring the number of use/sterilization cycles to which an instrument is subjected.

SUMMARY OF THE INVENTION

In accordance with the present invention, a method of indicating a sterilization life-span of an instrument is provided. A color coded marker is connected with the instrument. The color coded marker has a composition which is acted upon by the reactive component of fluid sterilants to change color. The color composition is formulated such that the color change occurs over a preselected number of cycles, which number of cycles are preselected in accordance with the requirements of the instrument.

In accordance with a more limited aspect of the present invention, a warning or caution label is provided in conjunction with the color change material such that the warning label becomes apparent within the preselected number of cycles.

In accordance with a more limited aspect of the present invention, the color change element is an integral portion of the instrument.

In accordance with another more limited aspect of the present invention, the sterilization fluid is a liquid solution containing a strong oxidant. The color change material includes a member which is impregnated with a pigment which changes color as it is oxidized.

In accordance with another more limited aspect of the present invention, a means is provided for controlling access of the sterilant solution to the color change composition.

One advantage of the present invention is that it provides an instrument carried indicator of remaining life-span of the instrument.

Another advantage of the present invention is that the indicator is updated or indexed without operator intervention.

Another advantage of the present invention is that it provides a ready indicator that the functionality of the instrument has not been compromised by over-use.

Other advantages of the present invention include its low cost and simplicity of use.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 4 illustrates a life-span color indicator in accordance with the present invention integrally connected with an instrument;

FIG. 5 is an exploded view illustrating an exemplary construction of the color indicator of FIG. 4; and, FIG. 6 illustrates an alternate embodiment of a color coded life-span indicator.

DETAILED DESCRIPTION OF THE PREFERRED EMBODIMENTS

Figure 1:
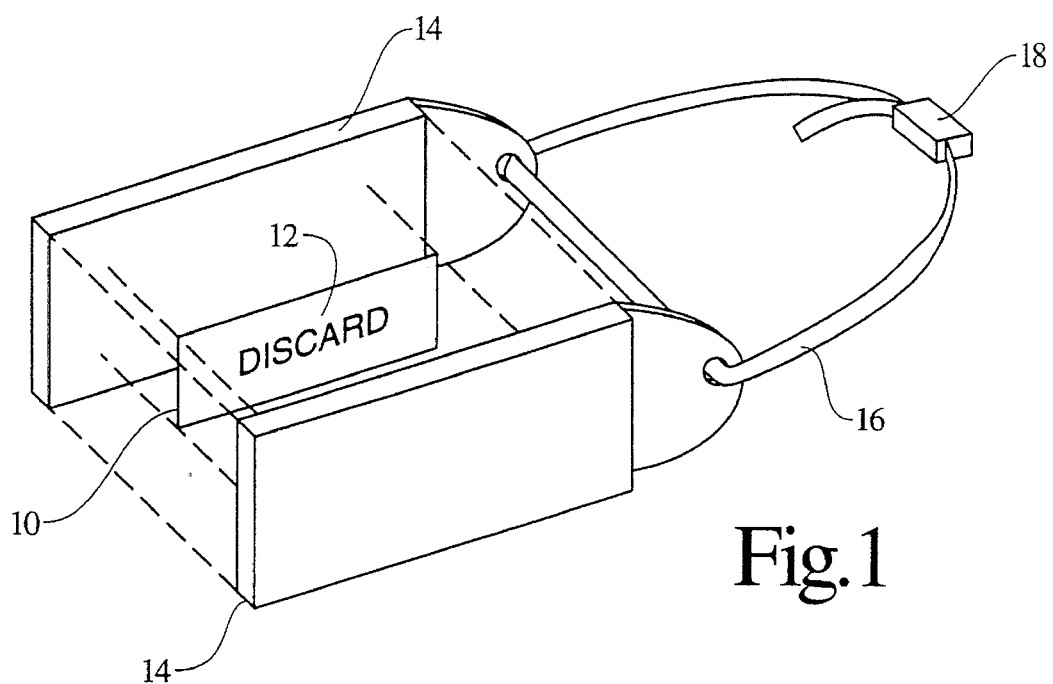
FIG. 1 is an exploded view of a tag in accordance with the present invention for attachment with an instrument.

With reference to FIG. 1, a label 10 carries an indicia 12 indicating that the associated instrument is to be reconditioned or discarded. Preferably, the label 10 is of an oxidation resistant material such as a thin film plastic. In the illustrated embodiment, the indicia 12 is a printed word indicating that it is time to recondition or discard the associated instrument. Preferably the word is printed with a pigment that is highly resistant to oxidation or, sealed against contact with oxidants. However, graphic symbols and other indicia are also contemplated.

The label 10 is laminated between two layers of pigment impregnated plastic 14. The layers are impregnated with a pigment material which changes color or opacity with exposure to a sterilization or other microbial decontamination fluid. An affixing means such as a plastic strap 16 is provided for affixing the tag to the associated instrument. Preferably, the strap has a slide clasp 18 with a one-way mechanism inside such that once the strap is tightened to the instrument, it cannot be removed without cutting the strap or destroying the strap or slide clasp.

The plastic layers 14 are constructed of a translucent material, such as polyvinylchloride (PVC), silicon rubber, or the like. The material is colored with a dye or pigment that changes color with exposure to the microbial decontamination fluid. In the preferred embodiment, the instrument is sterilized in an automated processor such as the one illustrated in U.S. Pat. Nos. 4,892,706 or 5,217,698. The microbial decontamination fluid is a liquid solution containing a strong oxidant, specifically peracetic acid. However, other liquid and gaseous fluids are also contemplated, including hypochlorite solutions, ethylene oxide gas, and the like.

The pigment may be any of various dyes, chromogens, and the like which change color as the result of exposure to a preselected time-concentration exposure of the sterilant or disinfectant fluid. Typically, organic pigments fade or lose their color with exposure to strong oxidants. Thus, as the pigment is exposed to the liquid or gas or to high temperature steam, the pigment fades allowing the warning indicia 12 on the label 10 to be read.

In one preferred embodiment, the polyvinylchloride layers 14 were immersed in a circulated dyeing solution. The dyeing solution is prepared by dissolving 105 mg of crystal violet in 100.0 ml of anhydrous ethanol. 15 g of ethylcellulose is dissolved in 400.0 ml of toluene. 25 ml of the crystal violet solution are mixed with 400 ml of the ethylcellulose solution and the mixture circulated over the polyvinylchloride strips for 42 minutes at ambient temperature. Excess dye is removed and the plastic strips dried. Thereafter, the plastic strips are baked at 37° C. in an incubator for 2 hours.

In addition to crystal violet and derivatives of pararosaniline other pigments, stains, dyes, chromogens, tinting agents and chemistries that upon reaction produce color changes may be used. These include certain food dyes, biological stains as phenazone based dyes such as safranine, and stains such as used in acid-base indicators.

Figure 2:
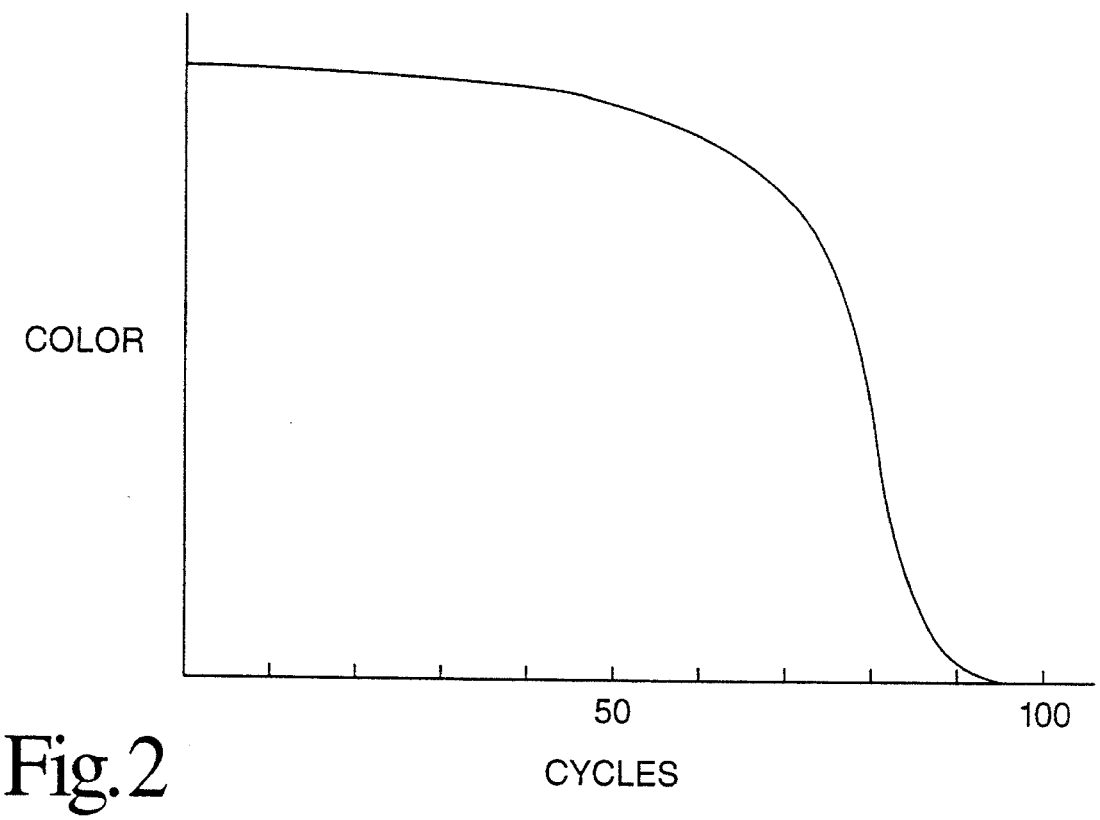
FIG. 2 is a diagrammatic illustration of color intensity versus number of cycles for one preferred embodiment of a color change composition of the present invention.

With reference to FIG. 2, for calibration and testing, the impregnated polyvinylchloride plastic material was subject to a multiplicity of 12 minute sterilization cycles with the above-referenced automated processor. In each cycle, the tag was immersed in a peracetic acid solution having an initial peracetic acid concentration of about 2000 ppm and a pH of about 6.5. The above described impregnated material showed little color change until after 40 sterilization cycles. By 95 cycles, the color was substantially gone.

Figure 3:
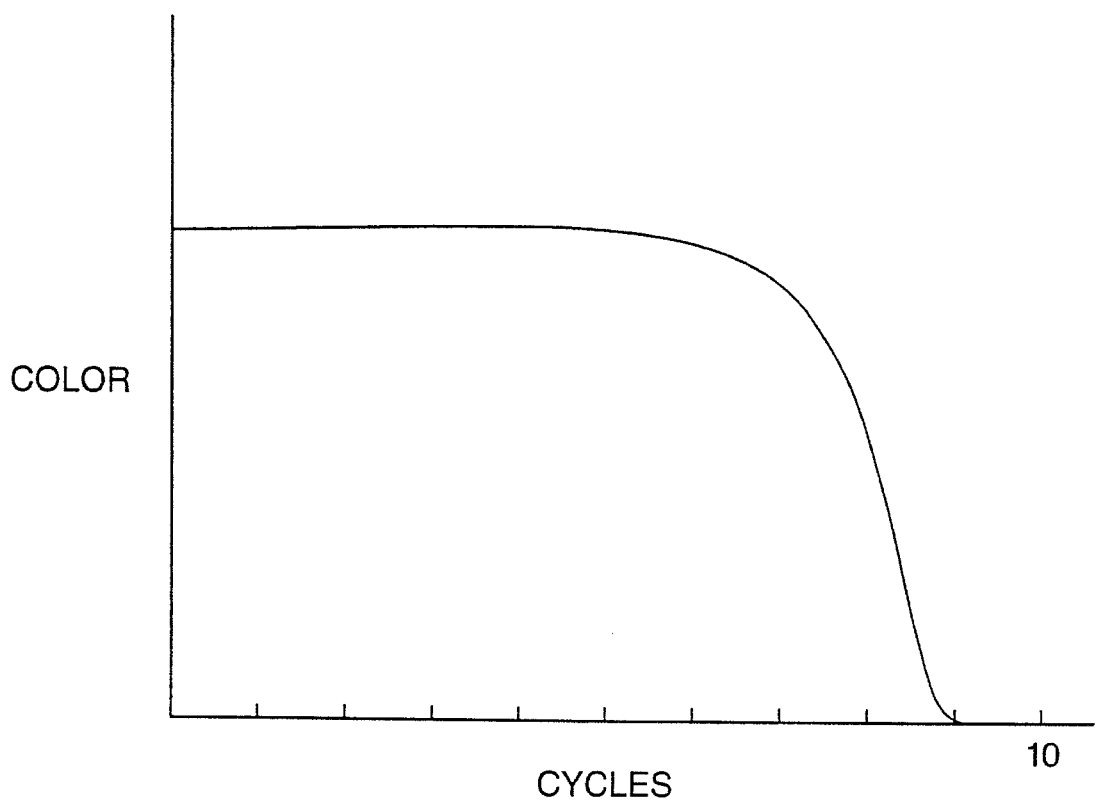
FIG. 3 is a diagrammatic illustration of color intensity versus number of cycles for another embodiment of the present invention.

Shorter use cycle indicators can also be designed. For example, 25 ml of the crystal violet/anhydrous ethanol solution is mixed with 400 ml of anhydrous ethanol. The tag is immersed in circulating solution for 5 minutes and dried. As illustrated in FIG. 3, the tinted plastic material started to show noticeable coloring change after only 7 cycles. By the end of 9 cycles, the plastic material completely lost its color.

Other pigments and solutions may be utilized. Similarly different baking durations and temperatures can be utilized to set the dye more or less strongly, hence to extend or shorten the number of cycles before the color is substantially lost. Other solution concentrations and soaking times are also contemplated. Extending the immersion duration or increasing the concentration tends to increase the number of cycles. Diluting the concentration and reducing the soaking time shortens the number of cycles.

In another embodiment, a 0.2% indicating dye solution was prepared by dissolving 2.0 g of crystal violet into 1.0 liter of tap water. This solution was mixed until completely dissolved and homogeneous. Porex brand porous open cell plastic foam plugs were then placed into test tubes, each containing approximately 10 ml of the dye solution. Inasmuch as the density of the plugs is less than that of the dye solution, two bath balls were added to each of the tubes to insure that the plugs remained completely submerged in the solution during the dying process. The test tubes were then placed into a test tube rack which was then placed into a vacuum desiccator. The vacuum pump was switched on and allowed to pull a vacuum in the desiccator for 20 minutes, following which the desiccator valve was closed to retain the vacuum after the vacuum pump was switched off. The plugs were then allowed to soak in the dye solution, under vacuum, for 2 hours, following which the vacuum on the desiccator was released. The plugs were then allowed to remain in the dye solution an additional 5 minutes before being removed from the dye. All transferring of the plugs was accomplished by means of forceps to insure that neither any dye was removed from the surface, nor was any finger oil, which might affect the uniformity of dye penetration, added to the surface of the plugs. The plugs were then placed into clean test tubes and dried in an incubator at 56° C. for approximately 3 hours.

Sixteen of the dyed plugs each attached to a vacustat clip to prevent them from floating in the sterilant, were then evenly dispersed on the fixation rack for the rigid tray. The fixation rack was then placed into a rigid container along with a commercial chemical indicator strip, also attached to a vacustat clip. The container was then placed within the processor tray and a peracetic acid sterilization cycle run. Following the cycle, the chemical indicator strip was removed and inspected for cycle completeness by comparing its color to the end point color block on the chemical indicator bottle. Four of the Porex plugs on the rack were chosen at random and removed from the container, with the remaining 12 plugs left undisturbed. A new chemical monitor strip, with a vacustat clip, was then placed into the container; a new cup of sterilant was added to the processor and a second processor cycle was initiated. While the second cycle was running in the processor, the four plugs which had just been removed from the processor, were sliced in half by means of a scalpel and forceps. The color of the internal surfaces of the plugs was compared to that of the outer surfaces. Both the outer surfaces and the inner, cut surfaces were inspected for degree and uniformity of dye penetration then their color was compared to the Fuller O'Brien Color Chip Chart for a color match. This procedure was repeated until all sixteen plugs had been removed from the sterilization processor, four per cycle, and inspected. At that point, four of the eight plugs which had not been exposed to sterilant in the processor were placed into the same processor in the same manner, but were exposed to a cycle in which no peracetic acid was used, solely builder. These four plugs represent a control for the possibility that rather than being bleached by the sterilant, the dye was washing out of the plugs by the action of the detergents or other components of the sterilant solution.

The results of the exposure of dyed Porex media plugs to peracetic acid sterilant processing is set forth in Table 1. Those plugs exposed to only one cycle with sterilant exhibited a uniform color on the outer surface. There was a discernible difference in color between those plugs exposed to one processor cycle with sterilant and the unprocessed controls which were dyed but which saw no exposure to either peracetic acid or builder. The same is true of those plugs exposed to two cycles with sterilant. The four plugs which were exposed to three processor cycles in the presence of peracetic acid sterilant exhibited a very faint, but nonetheless, detectable color on the outer surface. The inner surfaces, however, appeared uniform in color, and were the same color as the outer surface. Those plugs exposed to four cycles with sterilant were completely bleached on the outer surface. They appeared identical to the untreated plugs which had never been exposed to crystal violet dye. The inner surfaces of the four-cycle plugs were identical to the outer surface, i.e. completely bleached. In addition, these four plugs which had been exposed to the four sterilant cycles were lighter than any of the Fuller O'Brien color chips.

The color of the outer surfaces of the processor control plugs, which were exposed to one processor cycle in the presence of builder but not peracetic acid, did not match any of the Fuller O'Brien color chips. They were slightly lighter than the start block on the bottle label. When compared to the unprocessed plugs, dyed but not processed, which were the color of the start block on the bottle label, the inner surfaces of the builder-only control plugs did not exhibit uniform color, and their outer surfaces were also lighter in color, however, they were significantly darker purple than any of the plugs which had been processed with the peracetic acid sterilant.

TABLE 1

POROUS MEDIA LIFE-SPAN INDICATOR
CYCLE COUNT - COLOR CORRELATION

| CUMUL. CYCLES | FULLER O'BRIEN COLOR |
|---|---|
| 0 | * |
| 1 | 3-D54 |
|   | 1-D55 |
| 2 | 4-D115 |
| 3 | 4-D111 |
| 4 | ** |

\* - These dyed control plugs were exposed only to builders (no peracetic acid) in the processor. They are just perceptibly lighter than the unprocessed plugs.
\*\* - All four plugs were bleached white. Their white color was identical to that of the untreated factory plugs.

Thus, porous media can be successfully utilized as a cycle counter in the presence of peracetic acid based sterilant. Crystal violet dye applied to a porous media material will bleach to a degree dependent on the amount of dye present on the surfaces of the material, the concentration of peracetic acid in the sterilant, the flow rate of the sterilant, and the accumulated time of exposure to the sterilant. Inasmuch as the mean concentration of peracetic acid sterilant and its flow rate tend not to vary much from processor to processor and from cycle to cycle, a given amount of dye remaining within the porous media should be indicative of the number of cycles to which that cycle indicator has been exposed, this being a function of the accumulated exposure time of the dye to sterilant.

As another alternative, multiple layers can be added. For example, a clear coat may be applied over the indicator of Example 2. By selecting a coating with a predictable number of cycles before it reacts, the color change of the embodiment of FIG. 2 can be delayed the corresponding number of cycles. As another alternative, layers of different pigments can be applied such that rather than just fading in monochrome, the indicator changes color as the surface layer fades and an underlying layer is retained.

Other techniques for affixing the indicator to the instrument are also contemplated. With reference to FIG. 4, a medical instrument 20 such as an endoscope includes a ring 22 of the indicator material. For example, the instrument may have two portions which are threadedly interconnected adjacent to a recessed area in which the indicator ring 22 is mounted. Alternately, the ring can be heat shrunk onto the instrument. As shown in FIG. 5, an inner label 24 includes an indicia 26 such as the word "rebuild" or "discard". The ring 22 of the translucent, impregnable material surrounds the label exposing the indicia 26 as the impregnated color fades with repeated sterilization cycles.

With reference to FIG. 6, rather than using the color change indicator to obscure an indicia, the color itself can be used as the indicator. For example, a scale 30 has a portion 32 having the initial color of the color change material, a portion 34 having an intermediate color of the color change indicator, and a color indicator portion 36 denoting the color of the indicator 22 which indicates that the instrument should be discarded or rebuilt.

Various other structures for attaching a layer of the color changing instrument life-span indicator to the instrument may also be used. For example, the indicator may be painted on or coat a portion of the instrument. A functioning portion of the instrument may be constructed of the indicator plastic material. As another option, the region of the material which is impregnated with the color change indicator can be limited to a region having a preselected shape, such as the word "discard". The remainder of the material may be colored with a similar pigment which is insensitive to the oxidant or coated to protect it from the oxidant such that as the indicator region changes color, the word "discard" or another indicia becomes visible.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of indicating when to discontinue use of a multiple-use instrument which is designated to be used only a preselected plural number of times and which is sterilized or disinfected after each use, the method comprising:

affixing a color change material to the instrument which changes at least one of color and opacity with exposure to a preselected sterilant or disinfectant, the color change material being selected such that it undergoes a preselected color or opacity change after said preselected number of exposures to the preselected sterilant or disinfectant;

alternately using the instrument and sterilizing or disinfecting the instrument with the preselected sterilant or disinfectant;

after the color change material has undergone the preselected change indicating that the instrument has been subject to the preselected number of uses, discontinuing use of the instrument.

2. The method as set forth in claim 1 further including after discontinuing use of the instrument, rebuilding the instrument and affixing new color change material to the rebuilt instrument.

3. The method as set forth in claim 1 wherein the color change material changes from an opaque color to translucent and further including:

applying an indicia indicating that use of the instrument should be discontinued;

in the affixing step, affixing the color change material over the indicia, whereby after the preselected number of cycles, the color change material becomes sufficiently translucent for the user to view the indicia.

4. The method as set forth in claim 1 further including coloring a plastic with a dye which changes color with exposure to the sterilant or disinfectant and wherein the affixing step includes affixing the plastic material to the instrument.

5. The method as set forth in claim 1 wherein the instrument is sterilized or disinfected manually.

6. The method as set forth in claim 1 wherein the preselected sterilant or disinfectant includes a strong oxidant, the strong oxidant oxidizing the color change material to cause the color change.

7. The method as set forth in claim 6 wherein the sterilant solution includes peracetic acid.

8. The method as set forth in claim 7 wherein the color change material includes crystal violet.

9. The method as set forth in claim 1 wherein the sterilizing or disinfecting step includes immersing the item and the color change material into a fluid sterilant or disinfectant and circulating the fluid sterilant or disinfectant over all accessible surfaces thereof.

10. The method as set forth in claim 9 wherein the sterilant or disinfectant fluid is a liquid solution.

11. The method as set forth in claim 9 wherein the sterilant or disinfectant is a gas.

12. A method of indicating expiration of a life-span of an instrument which is sterilized or disinfected after each use in a processing cycle of an automated processor, the method comprising:

affixing a color change material to the instrument which changes at least one of color and opacity with each processing cycle of the automated processor, the color change material being selected such that it undergoes a preselected color or opacity change after being processed in preselected plural number of the processing cycles;

alternately (i) using the instrument and (ii) sterilizing or disinfecting the instrument and the color change material in the automated processor;

after the color change indicating the expiration of the life-span material has undergone said preselected change, discontinuing use of the instrument.

13. A method of determining when to discard an item which is subject to cycles of alternate use and microbial decontamination, the method comprising:

(a) affixing a material to the item which changes at least one of color and opacity with exposure to a preselected microbial decontamination fluid, the material being selected such that it undergoes a preselected opacity change after a preselected plural number of microbial decontamination cycles with the preselected microbial decontamination fluid in an automated processor;

(b) alternately using the item and microbially decontaminating the item and the material in the preselected microbial decontamination fluid in the automated processor;

(c) after the material has undergone the preselected opacity change indicating that the item has been subject to the preselected number of microbial decontamination cycles, discarding the item.

14. The method as set forth in claim 13 further including rebuilding the discarded item and repeating steps (a), (b), and (c) with the rebuilt item.

15. The method as set forth in claim 13 wherein the microbial decontaminating includes subjecting the item and the material to a strong oxidant for a preselected duration in the automated processor, the strong oxidant reacting with the material to change at least one of the material's color and opacity.

16. In a method in which a device is subject to cycles of alternate use and sterilization or disinfection processes in which processes internal and external surfaces of the device are brought into intimate contact with an antimicrobial fluid and which use or antimicrobial fluid degrades a component of the device such that the device should be discarded or rebuilt after a plural predetermined number of cycles, THE IMPROVEMENT COMPRISING:

affixing a color change indicator to the device, which color change indicator changes from an initial color or opacity to a predetermined color or translucency over the plural predetermined number of cycles, whereby the change of the color change indicator to the predetermined color or translucency provides a visual indication it is time to discard or rebuild the device;

discarding or rebuilding the device when the color change indicator changes to the predetermined color or translucency.

17. A tag for attachment to an instrument, the tag comprising:

a section of colorable material;

a substance which changes at least one of color and opacity after a preselected plural number of processing cycles by a sterilization or disinfection processor, the substance being incorporated into the material section;

a means for affixing the material section to an instrument.

18. A method of monitoring for expiration of a life-span of items subject to cycles of use and microbial decontamination, which items have a life-span defined by a preselected number of use and microbial decontamination cycles, the method comprising:

affixing a color change material to the item which changes at least one of color and opacity with each microbial decontamination, the color change material being selected such that it undergoes a preselected color or opacity change after a plural preselected number of said microbial decontaminations;

alternately using the item and microbially decontaminating the item and the color change material;

monitoring the color change material for the preselected change indicating that the item has been subject to the preselected plural number of use and microbial decontamination cycles that define the life-span of the item.

19. A method of counting a number of times which an device is used, the method comprising:

(a) affixing a color change material to the device, which color change material changes at least one of its color and opacity each time that the color change material is subject to an anti-microbial decontamination process, the color change material being selected such that it undergoes a preselected change of at least one of the color and opacity after a plural preselected number of anti-microbial decontaminations;

(b) using the device;

(c) after each use of the device, subjecting the device and the color change material to microbial decontamination; and, (d) repeating steps (b) and (c) alternately until the color change material undergoes said selected change which indicates that the device has been used said preselected number of times.

* * * * *